United States Patent
Pastusiak et al.

(10) Patent No.: US 9,128,025 B2
(45) Date of Patent: Sep. 8, 2015

(54) METHOD AND DEVICE FOR DETERMINING CHEMICAL AND/OR PHYSICAL PROPERTIES OF WORKING SUBSTANCES IN A MACHINE SYSTEM

(75) Inventors: Remigiusz Pastusiak, Munich (DE); Le Nga Quach, Hamburg (DE); Kerstin Wiesner, Putzbrunn (DE); Rainer Hartig, Buxtehude (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 300 days.

(21) Appl. No.: 13/389,978

(22) PCT Filed: Aug. 10, 2010

(86) PCT No.: PCT/EP2010/061571
§ 371 (c)(1),
(2), (4) Date: Feb. 10, 2012

(87) PCT Pub. No.: WO2011/018440
PCT Pub. Date: Feb. 17, 2011

(65) Prior Publication Data
US 2012/0140226 A1 Jun. 7, 2012

(30) Foreign Application Priority Data
Aug. 12, 2009 (DE) .......... 10 2009 037 240

(51) Int. Cl.
*G01J 3/28* (2006.01)
*G01N 21/25* (2006.01)
*G01N 21/85* (2006.01)
*G01N 21/00* (2006.01)
(Continued)

(52) U.S. Cl.
CPC ........ *G01N 21/0332* (2013.01); *G01N 21/3577* (2013.01); *G01N 21/05* (2013.01)

(58) Field of Classification Search
USPC .................................................. 356/300–334
See application file for complete search history.

(56) References Cited

U.S. PATENT DOCUMENTS

| | | | | |
|---|---|---|---|---|
| 4,681,443 A | * | 7/1987 | Bach et al. | 356/246 |
| 4,989,122 A | * | 1/1991 | Allekotte et al. | 362/97.1 |

(Continued)

FOREIGN PATENT DOCUMENTS

| | | | | |
|---|---|---|---|---|
| CN | 1373850 A | 10/2002 | | G01N 21/03 |
| CN | 1781017 A | 5/2006 | | G01N 21/05 |

(Continued)

OTHER PUBLICATIONS

International Search Report for PCT/EP2010/061571 dated Sep. 13, 2010.

(Continued)

*Primary Examiner* — Kara E Geisel
*Assistant Examiner* — Hina F Ayub
(74) *Attorney, Agent, or Firm* — Harness, Dickey & Pierce P.L.C.

(57) ABSTRACT

Methods and devices are disclosed for determining chemical and/or physical properties of working substances in a machine system, particularly in a floating device. In at least one embodiment, the working substance is irradiated with light, wherein the working substance has at least one temperature from a defined temperature range during irradiation; and the light penetrating the working substance or reflected by the working substance is spectrally analyzed.

26 Claims, 3 Drawing Sheets

(51) Int. Cl.
*G01N 21/03* (2006.01)
*G01N 21/3577* (2014.01)
*G01N 21/05* (2006.01)

(56) References Cited

U.S. PATENT DOCUMENTS

| | | | |
|---|---|---|---|
| 5,256,244 A * | 10/1993 | Ackerman | 427/162 |
| 5,407,830 A | 4/1995 | Altman et al. | 436/55 |
| 6,300,633 B1 | 10/2001 | Hunt et al. | 250/339.12 |
| 6,888,636 B2 * | 5/2005 | Martino et al. | 356/436 |
| 2005/0013740 A1 | 1/2005 | Mason et al. | 422/68.1 |
| 2005/0158461 A1 * | 7/2005 | Bescup et al. | 427/163.4 |
| 2006/0192122 A1 | 8/2006 | Chen et al. | 250/339.13 |
| 2006/0263893 A1 * | 11/2006 | Moses et al. | 436/143 |
| 2007/0059589 A1 | 3/2007 | Arasawa | 429/90 |
| 2008/0288182 A1 * | 11/2008 | Cline et al. | 702/24 |
| 2009/0290151 A1 * | 11/2009 | Agrawal et al. | 356/318 |
| 2010/0070197 A1 * | 3/2010 | Wang et al. | 702/22 |
| 2010/0164718 A1 * | 7/2010 | Parish et al. | 340/540 |
| 2010/0200104 A1 * | 8/2010 | Fleischer et al. | 141/1 |
| 2010/0245737 A1 * | 9/2010 | Aoyama et al. | 349/112 |

FOREIGN PATENT DOCUMENTS

| | | | |
|---|---|---|---|
| EP | 2 009 438 | 12/2008 | G01N 33/28 |
| JP | 05-215675 | 8/1993 | |
| JP | 2007-263893 A | 10/2007 | |
| WO | WO 00/17611 | 3/2000 | G01J 3/28 |
| WO | WO 2007/042051 | 4/2007 | G01N 33/28 |
| WO | WO 2007/093500 | 8/2007 | G01N 21/35 |
| WO | WO 2009/037089 | 3/2009 | G01N 33/28 |

OTHER PUBLICATIONS

EP Search Report for 10 2009 037 240.7 dated Mar. 5, 2010.
Korean Office Action dated Dec. 26, 2013 issued in Korean Application No. 10-2012-7006282 with English Translation.
Chinese Office Action dated Jun. 26, 2013 issued in Chinese Application No. 201080035814.9.
Office Action dated Jul. 11, 2014 issued in Korean Application No. 2012-7006282 with English Translation.

* cited by examiner

METHOD AND DEVICE FOR DETERMINING CHEMICAL AND/OR PHYSICAL PROPERTIES OF WORKING SUBSTANCES IN A MACHINE SYSTEM

PRIORITY STATEMENT

This application is the national phase under 35 U.S.C. §371 of PCT International Application No. PCT/EP2010/061571 which has an International filing date of Aug. 10, 2010, which designated the United States of America, and which claims priority to German patent application number DE 10 2009 037 240.7 filed Aug. 12, 2009, the entire contents of each of which are incorporated herein by reference.

FIELD

The invention generally relates to a method and/or a device for determining chemical and/or physical properties of operating substances in a machine installation, in particular in a floating entity.

BACKGROUND

A method and a device are known e.g. from WO 2009/037089 A1.

Accurate monitoring of chemical and/or physical properties of operating substances in machine installations is becoming increasingly important. This applies in particular to machine installations on board floating entities such as, e.g., ships or offshore platforms. For example, new EU directives have led to the introduction of sulfur limit values for ship fuels that must be complied with by ships in ports or in certain maritime or inland waterways. When traveling in said waters, ships can be subject to inspections to verify whether only fuel having a sulfur content below the prescribed limit value is being used.

On the world's oceans outside of these waters it continues to be permissible to burn fuel having any sulfur content. Low-sulfur fuel is more expensive than fuel with a high sulfur content, so ships are operated over the greatest part of the route with cheap sulfur-containing fuel and low-sulfur fuels are used only in areas subject to special limit values. This means that in the future ships will bunker fuels of different qualities and that said fuels will also be mixed with one another as necessary (a process referred to as "blending").

The new EU directives make the proper keeping of logbooks with details of fuel changeover a condition for ships being able to enter ports of the EU community. Samples of ship fuels can be taken during inspections and analyzed to determine their sulfur content. Ship personnel are therefore required not only to monitor the fuel supplied to the machines during operation, but also to check beforehand the quality of the fuel at the time of refueling.

A fuel system having a measuring and evaluation device for online determination of the sulfur content of the fuel with the aid of infrared spectroscopy is already known from WO 2009/037089 A1. For this purpose the fuel is irradiated in a measuring cell with light from an infrared (IR) light source. The spectrum of the light transmitted through the fuel or reflected by the fuel is measured by means of a spectrometer and the measured spectrum analyzed with the aid of algorithms and using a calibration model.

Already known from WO 2007/093500 A1 is a measuring system in which the sulfur content of a ship fuel is determined with the aid of IR spectroscopy and the lubricant supply to the cylinders of a combustion engine driven by means of said fuel is controlled as a function thereof.

In addition to determining the sulfur content in fuels there exists a need in many machine installations to determine chemical and/or physical properties of a plurality of other operating substances such as e.g. lubricants in bearings or hydraulic fluids as part of preventive maintenance measures or in order to optimize operation.

SUMMARY

In one embodiment, a method and/or device is provided to improve even further the degree of precision with which the chemical and/or physical properties of the operating substances are determined.

In one embodiment a method is provided for determining chemical and/or physical properties of operating substances in a machine installation, in particular in a floating entity such as e.g. a ship or an offshore platform. In one embodiment, the operating substance is irradiated with light; and light transmitted through the operating substance or reflected by the operating substance is spectrally analyzed. In the course of the irradiation the operating substance has in one embodiment at least a temperature from a predefined temperature range, preferably exactly a predefined temperature.

In another embodiment a device is provided for determining chemical and/or physical properties of operating substances in a machine installation, in particular in a floating entity such as e.g. a ship or an offshore platform. In one embodiment, the device has a measuring and evaluation device comprising a light source for irradiating an operating substance with light and having a spectrometer for spectral analysis of light transmitted through the operating substance or reflected by the operating substance; and has a heating device for heating the operating substance and/or a cooling device for cooling the operating substance at least to a temperature from a predefined temperature range, preferably exactly to a predefined temperature.

BRIEF DESCRIPTION OF THE DRAWINGS

Embodiments of the invention are explained in more detail below with reference to example embodiments illustrated in the figures, in which.

DETAILED DESCRIPTION

Figure 1:
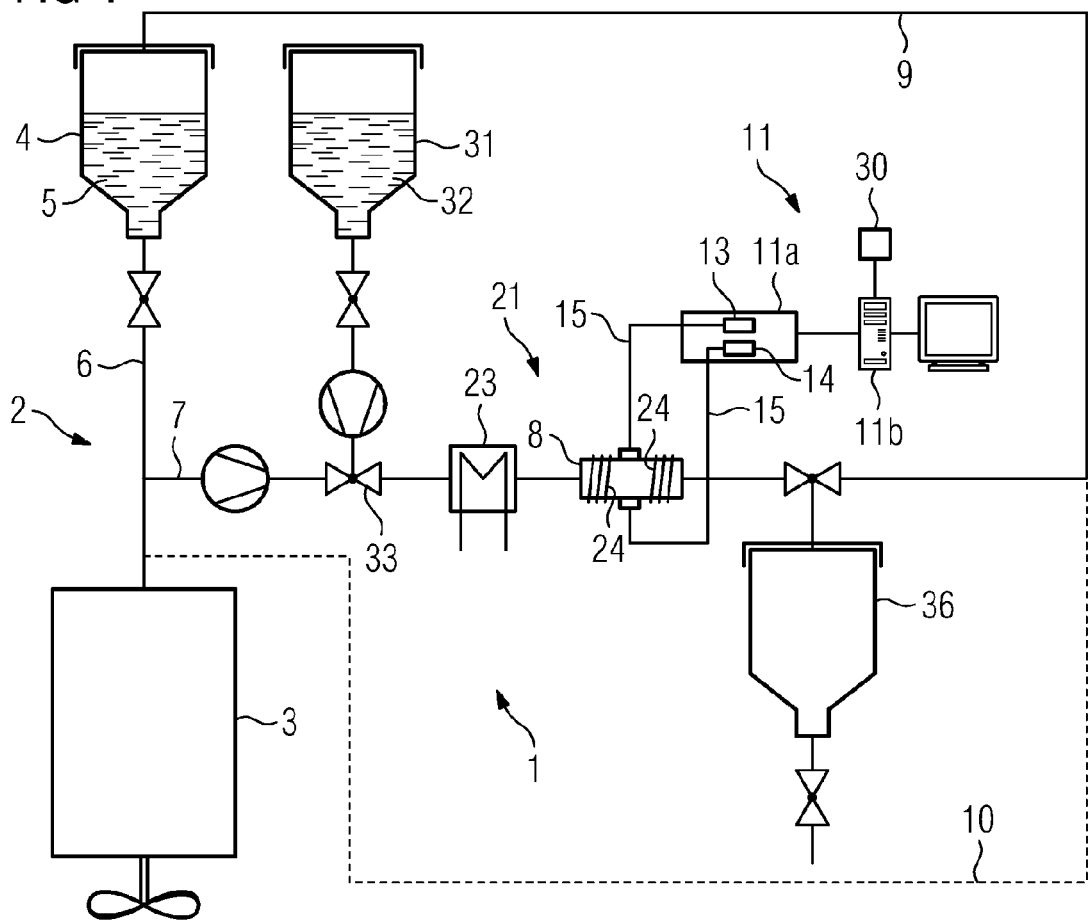
FIG. 1 shows a device according to an embodiment of the invention.

In one embodiment a method is provided for determining chemical and/or physical properties of operating substances in a machine installation, in particular in a floating entity such as e.g. a ship or an offshore platform. In one embodiment the operating substance is irradiated with light; and light transmitted through the operating substance or reflected by the operating substance is spectrally analyzed. In the course of the irradiation the operating substance has in one embodiment at least a temperature from a predefined temperature range, preferably exactly a predefined temperature.

This approach is based on the knowledge that varying ambient temperatures such as are present, e.g., in machine installations on board floating entities which operate in both tropical and arctic waters, or in installations that are subject to extreme daytime/nighttime variations in ambient temperature can lead to different temperatures of the operating substance when the latter is irradiated with light. However, the intensity of the light transmitted through the operating substance or reflected by the operating substance has a not inconsiderable dependence on temperature which can then lead to inaccuracies in the evaluation of the spectra. Varying temperatures also have an effect on other physical parameters such as the viscosity, density and hence flow velocity of the operating substance, which can likewise lead to inaccuracies in the evaluation of the spectra. If, on the other hand, the operating substance, when irradiated, has at least a temperature from a predefined temperature range, preferably exactly a predefined temperature, substantially identical or preferably exactly identical general conditions can always be created for the spectral analysis and the evaluations following on therefrom and consequently the degree of precision in determining the chemical and/or physical properties can be increased.

By "physical properties" in this context are understood properties which relate to the operating substance per se, i.e. not just to individual substances contained in the operating substance. Examples of these are the viscosity, density and flash point. By "chemical properties" are understood properties that are outside of the definition range of the physical properties and relate to the chemical composition of the operating substance such as, e.g., type and proportion of its constituent substances (e.g., content in terms of water, sulfur or ash), cetane number or pH value. In this case the physical properties can usually be derived from the chemical properties.

The operating substance can be any substance in connection with the operation of the machine installation, such as, e.g., fuel, propellant, lubricant, coolant or hydraulic fluid.

If, prior to the irradiation, the operating substance does not have the desired temperature from the predefined temperature range or the predefined temperature, the substance can be heated or cooled to a temperature from the predefined temperature range, preferably to the predefined temperature, before being irradiated with the light.

As has become apparent, a sufficiently good degree of precision in determining the chemical and/or physical properties can be achieved for most application situations when the predefined temperature range equals a maximum of 10 K.

According to a particularly advantageous embodiment a plurality of in each case different chemical and/or physical properties of the operating substance are determined in the spectral analysis of the light with the aid of a plurality of different algorithms. For this purpose an algorithm can be stored for example in an evaluation unit for each of the properties to be determined, each such algorithm in turn using a calibration model in each case, as described e.g. in WO 2009/037089 A1. A plurality of properties of the operating substance can therefore be determined simultaneously with just a single measurement and consequently with only a small investment in extra equipment.

The operating substance is preferably irradiated with light in a measuring cell through which the operating substance flows. A measuring cell of said kind can be implemented in a compact design and be installed either directly into the pipework system of the machine installation or into an additional bypass line. Particularly accurate and reliable measurements are possible here if the measuring cell is embodied as a transmission measuring cell.

The accuracy of the measurements can be increased still further by cleaning the measuring cell, for example at regular time intervals, by means of a cleaning fluid. For this purpose the supply of operating substance to the measuring cell is preferably cut off and the cleaning fluid passed through the measuring cell instead of the operating substance. Deposits in the measuring cell which can result for example due to a relatively long shutdown or following a long period of continuous operation and which can adversely affect the measurements can be removed by this means.

The cleaning fluid can also be used as a reference medium for verifying that the measuring cell is operating correctly. For this purpose the cleaning fluid can be irradiated with light, exactly as in normal operation, as the fluid flows through the measuring cell, and light transmitted through the cleaning fluid or reflected by the cleaning fluid can be subjected to spectral analysis. The spectrum obtained in the analysis can be compared with a reference spectrum for the cleaning fluid. If deviations from the reference spectrum are present, these indicate deficiencies in the general conditions for the measurements (e.g. signs of attrition or deposits in the measuring cell).

The determined chemical and/or physical properties of the operating substance are advantageously used for controlling the operation of the machine installation. This can be accomplished for example by incorporating them into an automation or monitoring system of the machine installation. The operation of the installation can be optimized as a result. Furthermore, machine parts can be monitored for wear and tear and maintenance or repair measures initiated at an early stage or maintenance intervals optimized.

According to a further advantageous embodiment the chemical and/or physical properties determined for the operating substance at a specific time instant are assigned a time and location specification. This enables the acquired data to be logged for control and monitoring purposes (e.g. to prove a correct quality of fuel to authorities) or for more extensive analyses (e.g. cost/benefit analyses, trend analyses, fuel quality analyses, distance calculations).

In another embodiment, a device is provided for determining chemical and/or physical properties of operating substances in a machine installation, in particular in a floating entity such as e.g. a ship or an offshore platform. In one embodiment, the device has a measuring and evaluation device comprising a light source for irradiating an operating substance with light and having a spectrometer for spectral analysis of light transmitted through the operating substance or reflected by the operating substance and has a heating device for heating the operating substance and/or a cooling device for cooling the operating substance at least to a temperature from a predefined temperature range, preferably exactly to a predefined temperature.

The advantages cited for the method according to the invention apply analogously to the device according to the invention.

FIG. 1 shows in a simplified schematic diagram a device 1 for determining chemical and/or physical properties of an operating substance of a machine installation 2. The machine installation 2 comprises for example a combustion engine 3 and a tank 4 in which an operating substance of the combustion engine 3, for example a fuel 5 of the combustion engine 3, is stored. The machine installation 2 is for example a driving powerplant on board a ship. The combustion engine 3 is then for example a large diesel engine for driving the ship and the fuel 5 is diesel fuel.

Branching off from a fuel feed line 6 from the tank 4 to the engine 3 is a line 7 via which some of the fuel 5 is supplied to a measuring cell 8. From the measuring cell 8 the fuel is either returned to the tank 4 by way of a line 9 or alternatively fed back into the line 6 by way of a line 10.

Figure 2:
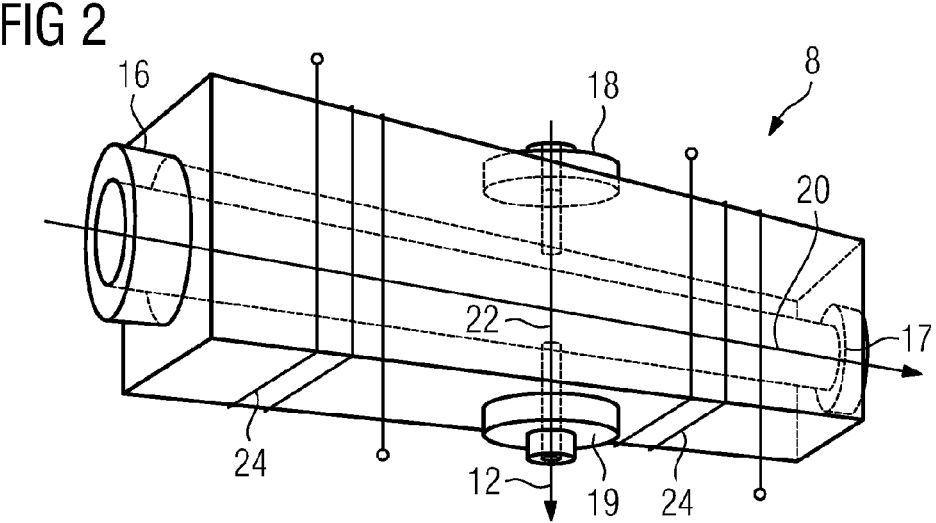
FIG. 2 shows a transmission throughflow cell.

The measuring cell 8, together with a measuring and evaluation device 11, constitutes the core of an arrangement such as that described e.g. in WO 2009/037089 A1. The measuring and evaluation device 11 comprises a measuring unit 11a having an IR light source 13 and an IR spectral analyzer 14 which are connected via fiber optic cables 15 to the measuring cell 8, and an evaluation unit 11b in the form of a computer having a display device for evaluating the spectra measured by the IR spectral analyzer 14 and for controlling the measuring unit 11a. The measuring cell 8 is preferably embodied as a transmission throughflow measuring cell, as illustrated by way of example in FIG. 2. The fuel is supplied to the measuring cell 8 via an inlet 16 and discharged via an outlet 17. Inside the measuring cell 8 the fuel flows in the flow direction 20 from the inlet 16 to the outlet 17. Arranged on two opposite walls of the measuring cell 8 at right angles to the flow direction 20 of the fuel are terminals 18, 19 for the fiber optic cables 15, the terminal 18 being connected via a fiber optic cable 15 to the IR light source 13 and the terminal 19 being connected via a fiber optic cable 15 to the IR spectral analyzer 14. By means of this arrangement the fuel is irradiated by way of the inlet 18 with IR light of the IR light source 11 and light transmitted through the fuel in the direction 12 is supplied via the outlet 19 to the IR spectral analyzer 14 and spectrally analyzed there.

In one embodiment, the device 1 also includes a heating device 21 which comprises a heating element in the form of a heat exchanger 23 arranged in the flow direction of the fuel upstream of the measuring cell. The heating device 21 additionally comprises second heating elements in the form of heating coils 24 which are arranged on or in the measuring cell 8. Prior to the irradiation the fuel is heated by means of the heating device 21 to a predefined temperature of e.g. 65° C., so that during the irradiation it has the same predefined temperature at all times and consequently also the same density, viscosity and flow velocity. If necessary a cooling device for cooling the fuel to the predefined temperature may also be present instead of a heating device. Toward that end the heating device 21 or the cooling device can include an open- and/or closed-loop control unit which measures the temperature of the fuel by way of a sensor and as a function thereof controls and/or regulates the heating capacity of the heating device 21 or the cooling capacity of the cooling device in such a way that during the irradiation the fuel always has the desired predefined temperature.

A plurality of different algorithms for determining a plurality of in each case different chemical and/or physical properties of the fuel are stored in the evaluation unit 11b. For this purpose an algorithm is stored in the evaluation unit 11b for each of the properties to be determined, each such algorithm in turn using a separate calibration model in each case, as described e.g. in WO 2009/037089 A1. A plurality of chemical properties of the fuel (e.g. water content, sulfur content, cetane number) and a plurality of physical properties (e.g. viscosity, density, flash point) can therefore be determined simultaneously on the basis of a single spectrum, i.e. with just a single measurement, and consequently with just a single measuring cell 8, which properties can be processed further in the evaluation unit 11b, displayed and stored.

The evaluation unit 11b is coupled to a GPS receiver 30 and assigns the data concerning chemical and/or physical properties that has been ascertained for an operating substance at a specific time instant a time and location specification which is stored with said data.

In another embodiment, the device 1 additionally includes a reservoir 31 containing a cleaning fluid 32 (e.g. pure diesel fuel). The reservoir 31 can be connected to the measuring cell 8 via a two-way valve 33 such that either fuel 5 from the tank 4 or cleaning fluid 32 from the reservoir 31 can be passed through the measuring cell 8. Deposits in the measuring cell 8 which can result for example due to a relatively long shutdown or following a long period of continuous operation and which can adversely affect the measurements can be removed by cleaning the measuring cell 8 by means of the cleaning fluid.

The cleaning fluid 32 can also be used as a reference medium for verifying that the measuring cell 8 is operating correctly. For this purpose the cleaning fluid can be irradiated with light, exactly as in normal operation, as the fluid flows through the measuring cell 8, and light transmitted through the cleaning fluid or reflected by the cleaning fluid can be spectrally analyzed. The spectrum obtained in the analysis can be compared with a reference spectrum for the cleaning fluid. If deviations from the reference spectrum are present, these indicate deficiencies in the general conditions for the measurements (e.g. signs of attrition or deposits in the measuring cell 8).

After flowing through the measuring cell 8 the cleaning fluid is either supplied to the engine 3 by way of the line 10 or else stored in a reservoir 36, from where it is disposed of further.

Figure 3:
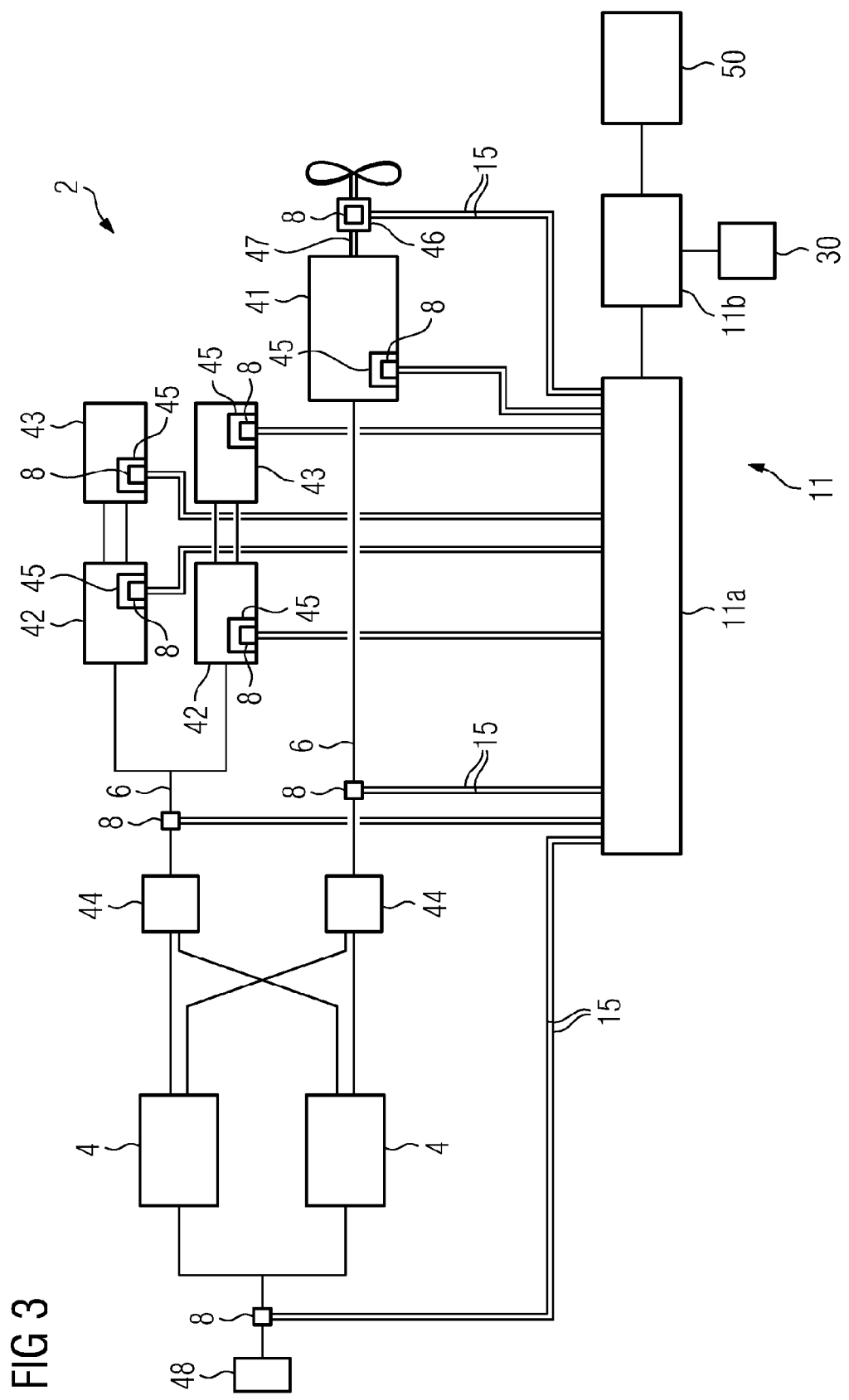
FIG. 3 shows a first device for analyzing a plurality of operating substances of a machine installation.

As shown in FIG. 3, the device 1 can also include a plurality of measuring cells 8 for determining chemical and/or physical properties of a plurality of operating substances of a machine installation 2 and/or of the same operating substance at a plurality of different points of the machine installation 2 which are or can be connected to the (central) measuring and evaluation device 11 via fiber optic cables 15.

In the case of a ship, for example, one measuring cell 8 in each case can be arranged in the fuel feed lines 6 to a diesel engine 41 for driving the ship 3 and to diesel engines 42 for driving generators 43 for generating power for the ship's onboard electricity grid. In this arrangement the measuring cells 8 are disposed in the line 6 after homogenizers 44 of a mixing device (not shown in further detail) via which fuels of different quality that are stored in the tanks 4 are mixed (in a process called "blending").

One measuring cell 8 in each case is also stored in the lubricant supplies 45 of all the machines of the machine installation (i.e. the diesel engines 41 and 42 and the generators 43) as well as in the lubricant supply of a bearing 46 of a propeller shaft 47.

A further measuring cell 8 is located after a tank filler neck 48 for filling the tanks 4 of the ship with fuel and serves for monitoring the quality of the fuel during the refueling of the ship.

The (central) measuring and evaluation device 11 is in this case coupled to an automation system 50 of the machine installation 2 in order to enable the determined chemical and/or physical properties to be used for controlling the operation of the machine installation. For example, the maintenance intervals can be adjusted if an increase in heavy metals in a lubricant is detected. The automatic switchover between fuels of different quality upon reaching zones subject to special requirements (e.g. ports) can be optimized. The machines can be monitored automatically for wear and tear and can be switched off if necessary. Continuous logging of all relevant properties of the operating substances can serve as a basis for a cost/benefit analysis of the fuel in the tanks for quality assessment purposes and forecasts in respect of fuel consumption and remaining distances to travel with current tank fuel reserves can be calculated. The acquired data can also be integrated into trend analyses within the automation system. The possibility of logging the acquired data for control and monitoring purposes (e.g. to provide proof to authorities) is particularly important. It is of particular advantage here that with the aid of the described device the chemical and/or physical properties of an operating substance can be determined "online", i.e. without great delay, thereby enabling a very timely response to be made to unwelcome events.

Figure 4:
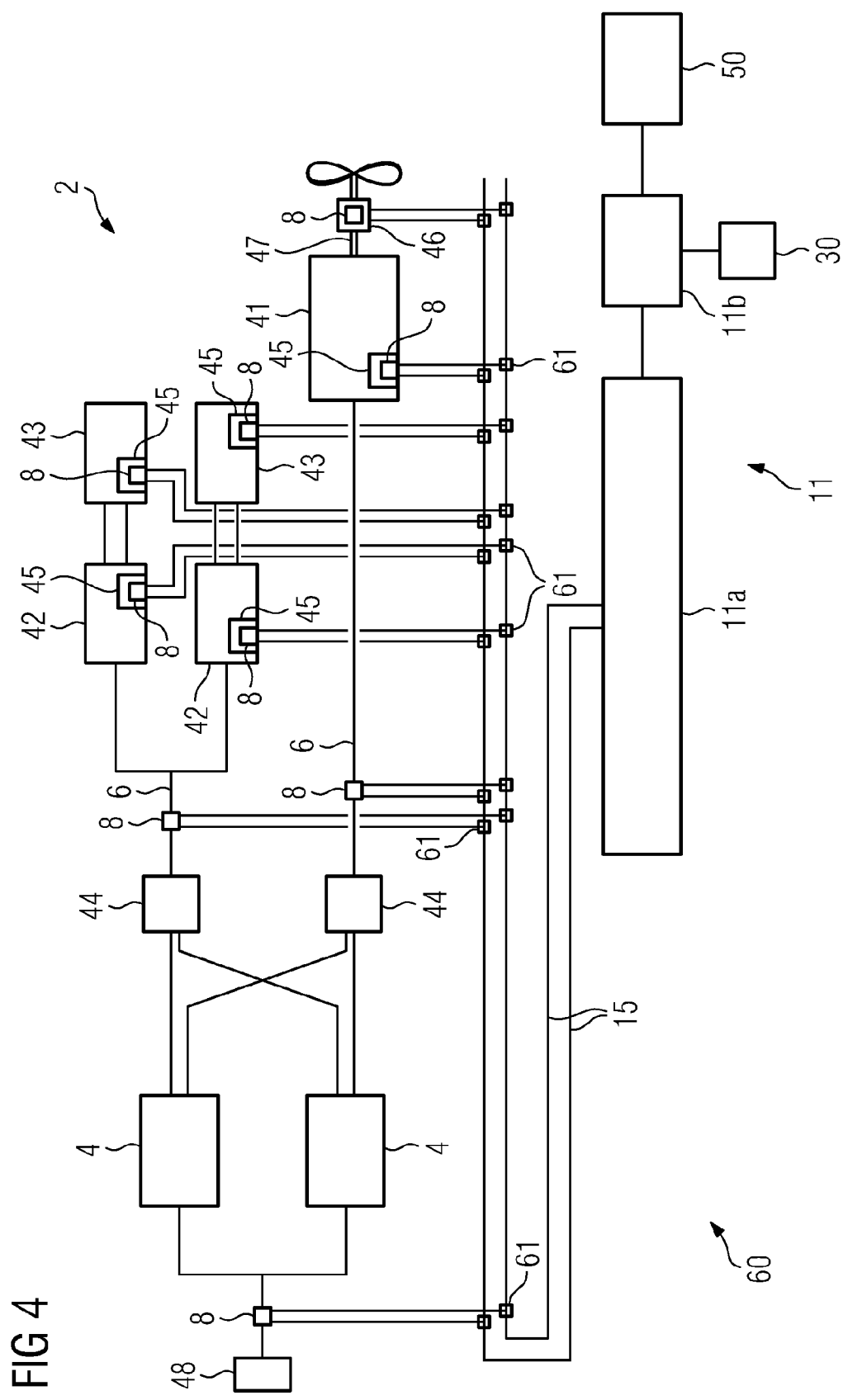
FIG. 4 shows a second device for analyzing a plurality of operating substances of a machine installation.

In order to reduce the number of fiber optic cables 15 required, the measuring unit 11a can—as shown in FIG. 4—also be connected to the individual measuring cells 8 via a multiplexer system 60 consisting of two central fiber optic cables 15 which are connected to the measuring unit 11a and of a plurality of multiplexers 61, each of the measuring cells 8 being connected via one multiplexer 61 in each case to each of the two central fiber optic cables 15.

In a further alternative embodiment the measuring and evaluation device 11 can also be implemented as a transportable instrument which is connected as necessary locally at the site of a measuring cell 8 via fiber optic cables 15 to the measuring cell 8.

The invention claimed is:

1. A method for determining chemical and/or physical properties of at least one operating substance in a ship, the method comprising:
   irradiating the at least one operating substance with light, wherein the at least one operating substance includes at least a temperature from a defined temperature range during the irradiation;
   spectrally analyzing the light transmitted through the at least one operating substance or reflected by the at least one operating substance;
   wherein a time specification and a location specification are assigned to the chemical and/or physical properties determined for the at least one operating substance at a specific time instant;
   wherein the chemical and/or physical properties determined for the at least one operating substance are used for controlling the operation of the ship and
   wherein the operation of the ship comprises driving the ship and/or driving at least one generator for generating power for the ship.

2. The method as claimed in claim 1, wherein prior to the irradiating, the at least one operating substance is heated or cooled to the temperature from the defined temperature range.

3. The method as claimed in claim 1, wherein the defined temperature range is equal to a maximum of 10 K.

4. The method as claimed in claim 1, wherein in the course of the spectrally analyzing, a plurality of different chemical and/or physical properties of the at least one operating substance are determined with the aid of a corresponding plurality of different algorithms.

5. The method as claimed in claim 1, wherein the at least one operating substance is irradiated with light in at least one measuring cell through which the at least one operating substance flows.

6. The method as claimed in claim 5, wherein the at least one measuring cell is cleaned by way of a cleaning fluid.

7. The method as claimed in claim 6, wherein the cleaning fluid is used as a reference medium for verifying that the at least one measuring cell is operating correctly.

8. A device for determining chemical and/or physical properties of at least one operating substance in a ship, comprising:
   a measuring and evaluation device including a light source for irradiating the at least one operating substance with light;
   a spectrometer capable of spectrally analyzing light transmitted through the at least one operating substance or reflected by the at least one operating substance;
   at least one of a heating device for heating the at least one operating substance and a cooling device for cooling the at least one operating substance at least to a temperature from a defined temperature range;
   wherein the measuring and evaluation device is coupled to a GPS receiver for assigning a time specification and a location specification to the chemical and/or physical properties determined for the at least one operating substance at a specific time instant;
   wherein the measuring and evaluation device is coupled to an automation system of the ship for using the chemical and/or physical properties determined for the at least one operating substance for controlling the operation of the ship and
      wherein the operation of the ship comprises driving the ship and/or driving at least one generator for generating power for the ship.

9. The device as claimed in claim 8, wherein the defined temperature range equals a maximum of 10 K.

10. The device as claimed in claim 8, wherein a plurality of different algorithms are stored in the measuring and evaluation device for determining a plurality of in each case different chemical and/or physical properties of the at least one operating substance from a single spectrum.

11. The device as claimed in claim 8, wherein the at least one operating substance is irradiated with light in at least one measuring cell through which the at least one operating substance flows.

12. The device as claimed in claim 11, further comprising:
   a reservoir containing a cleaning fluid, wherein the reservoir is connectable to the at least one measuring cell.

13. The device as claimed in claim 8, further comprising:
   a plurality of measuring cells for determining chemical and/or physical properties of a plurality of different operating substances of the ship and/or of the same operating substance at a plurality of different points of the ship which are connected or are connectable to the measuring and evaluation device via fiber optic cables.

14. The method as claimed in claim 1, wherein the at least one operating substance includes a defined temperature during the irradiation.

15. The method as claimed in claim 2, wherein the at least one operating substance is heated or cooled to the defined temperature.

16. The method as claimed in claim 5, wherein the at least one measuring cell is a transmission measuring cell.

17. The device as claimed in claim 8, wherein the at least one operating substance is heated or cooled to a defined temperature.

18. The device as claimed in claim 11, wherein the at least one measuring cell is a transmission measuring cell.

19. The method as claimed in claim 1, wherein the at least one operating substance is selected from the group consisting of a fuel, a propellant, a lubricant, a coolant and a hydraulic fluid.

20. The method as claimed in claim 1, wherein the at least one operating substance is a fuel supplied to a diesel engine for driving the ship and/or a fuel supplied to at least one diesel engine for driving the at least one generator for generating power for the ship.

21. The method of claim 1, wherein the at least one operating substance is lubricant supplied to a diesel engine for driving a ship and/or to at least one diesel engine for driving the at least one generator.

22. The method as claimed in claim 1, wherein the at least one operating substance is a fuel and the operation of the ship further comprises monitoring the quality of the fuel during refueling of the ship.

23. The device as claimed in claim 8, wherein the at least one operating substance is selected from the group consisting of a fuel, a propellant, a lubricant, a coolant and a hydraulic fluid.

24. The device as claimed in claim 8, wherein two measuring cells are present, wherein a first measuring cell is arranged in a fuel field line to a diesel engine for driving the ship and a second measuring cell is arranged in a fuel field line to at least one diesel engine for driving the at least one generator for generating power for the ship.

25. The device of claim 24, wherein the diesel engine for the driving the ship and/or the at least one diesel engine for driving the at least one generator comprise a further measuring cell within a lubricant supply.

26. The device as claimed in claim 8, wherein the at least one operating substance is fuel and the operation of the ship further comprises monitoring the quality of fuel during refueling of the ship.

\* \* \* \* \*